US 8,401,870 B2

(12) United States Patent  
Whelchel et al.

(10) Patent No.: US 8,401,870 B2  
(45) Date of Patent: Mar. 19, 2013

(54) SYSTEMS, METHODS, APPARATUSES, AND COMPUTER PROGRAM PRODUCTS FOR GENERATING PATIENT TIMELINES

(75) Inventors: Catherine Whelchel, Spartanburg, SC (US); Becky Ralston, Lafayette, CO (US); Melissa Roberts, Boulder, CO (US); Melissa Cummings, Boulder, CO (US); Josef Pusedu, Boulder, CO (US); Dianne Koepping, Lafayette, CO (US); David Williams, Minneapolis, MN (US)

(73) Assignee: McKesson Financial Holdings

( * ) Notice: Subject to any disclaimer, the term of this patent is extended or adjusted under 35 U.S.C. 154(b) by 340 days.

(21) Appl. No.: 12/365,681

(22) Filed: Feb. 4, 2009

(65) Prior Publication Data

US 2010/0198619 A1 Aug. 5, 2010

(51) Int. Cl.
*G06Q 10/00* (2012.01)
*G06Q 50/00* (2012.01)

(52) U.S. Cl. ............................... 705/2; 705/3
(58) Field of Classification Search ............... 705/2–3
See application file for complete search history.

(56) References Cited

U.S. PATENT DOCUMENTS

| | | | | |
|---|---|---|---|---|
| 5,740,428 A | * | 4/1998 | Mortimore et al. | 1/1 |
| 7,860,729 B2 | * | 12/2010 | Stangel | 705/2 |
| 2006/0206013 A1 | * | 9/2006 | Rothman et al. | 600/300 |
| 2006/0265249 A1 | * | 11/2006 | Follis et al. | 705/3 |
| 2007/0143143 A1 | * | 6/2007 | Villasenor et al. | 705/2 |
| 2008/0086328 A1 | | 4/2008 | Hertel et al. | |
| 2008/0086329 A1 | | 4/2008 | Hertel et al. | |
| 2008/0086330 A1 | | 4/2008 | Hertel et al. | |
| 2008/0086332 A1 | | 4/2008 | Hertel et al. | |
| 2008/0086333 A1 | | 4/2008 | Hertel et al. | |
| 2008/0086334 A1 | | 4/2008 | Hertel et al. | |
| 2009/0055735 A1 | * | 2/2009 | Zaleski et al. | 715/700 |

* cited by examiner

*Primary Examiner* — Joseph Burgess
(74) *Attorney, Agent, or Firm* — Alston & Bird LLP

(57) ABSTRACT

An apparatus and system are provided for generating one or more patient timelines corresponding to a patient(s). The apparatus includes a processor configured to receive medical information, associated with a patient(s), from one or more different computer systems and store the received medical information in a memory. The processor is configured to examine the received medical information stored in the memory and identify whether data in the medical information indicates the medical information corresponds to a patient(s). The data may include a unique identifier(s) (ID(s)) associated with a patient(s). The processor is also configured to determine if content in the received medical information is designated for inclusion in at least one graphical representation. The content may include one or more unique codes. The processor is also configured to generate a graphical representation(s) corresponding to a chronological sequence of medical events associated with a patient(s) during a period of time.

22 Claims, 11 Drawing Sheets

SYSTEMS, METHODS, APPARATUSES, AND COMPUTER PROGRAM PRODUCTS FOR GENERATING PATIENT TIMELINES

TECHNOLOGICAL FIELD

Embodiments of the invention relate generally to systems, methods, apparatuses and computer program products for facilitating an efficient mechanism in which to represent or depict a patient's medical care pertaining to one or more medical events or procedures that have occurred or are planned to occur during a patient's stay within a medical health facility.

BACKGROUND

Providing health care is becoming more complicated and staying apprised of a patient's medical status is oftentimes difficult. Today, medical personnel may rely on a variety of methods to remain informed of their patients' condition. For instance, currently, in order to access medical information associated with a patient(s) admitted to a health care facility, medical personnel (e.g., clinicians) typically may obtain relevant medical information (e.g., surgeries, transfers between medical units, laboratory test results, etc.) from a variety of clinical applications and flowsheets. The relevant information about a patient (surgeries, transfers between medical units, laboratory test results, etc.) is generally scattered throughout a patient record. Some information can be obtained and analyzed by utilizing an electronic flowsheet or a grid layout. These grids may show time across the top of a page and tasks or history associated with medical data across the bottom of a page. Additionally, medical personnel may utilize other parts of the patient chart such as documentation, assessments or Progress Note information to obtain relevant medical information associated with a patient(s) admitted to a health care facility. In either method, it can be difficult and time consuming for the clinician to put together a "patient story" of how the patient has progressed during the current visit.

However, it is typically difficult for medical personnel to easily identify relevant medical information corresponding to a patient(s), such as how patients have responded to certain medications, for example, or whether their vital signs have responded to certain medications, because clinicians typically have to search and evaluate lots of data to find relevant information associated with a patient. As such, using grids or flow sheets to identity relevant medical information associated with a patient may result in inefficiencies within a health care facility due to the time that it takes to retrieve and locate relevant information and due to the information that is not available on the grid or flowsheet. Moreover, the use of grids or flow sheets may create opportunities for medical personnel to make mistakes or errors which may result in deterioration of a patient's health since medical personnel typically would be required to search and evaluate substantial amounts of data when using a grid or flow sheet as described above.

Additionally, using grids and flow sheets, as well as other existing mechanisms, do not provide an easy manner in which medical personnel may obtain a picture or summary view of a patient's health or determine a patient's status or progress in their care, for example determining what surgeries that a patient(s) had, determining when the surgeries occurred, and/or identifying key medical events that have occurred regarding the patient(s) at glance. Furthermore, sorting through different applications or different pages is time consuming and may provide an opportunity for medical personnel to make errors.

Thus, a need exists to provide a more efficient mechanism of gathering or retrieving medical information associated with one or more patients and compiling that medical information and providing the medical information in a picture or summary view so that medical personnel can more easily determine when medical events or procedures associated with a patient(s) have occurred or are planned to occur some time in the future. Additionally, a need exists to summarize clinical data for a quick picture of a patient(s) status and story.

BRIEF SUMMARY

One or more exemplary embodiments may provide a health care professional with an easy and efficient mechanism of viewing a patient's acute care length of stay within a medical facility (e.g., hospital) and identifying one or more events or procedures (e.g., surgeries, laboratory results, medical tests, transfers between medical units, etc.) that have occurred at specified times or are planned to occur at specified times in the future while the patient is admitted to the medical facility. In this regard, the exemplary embodiments may provide an at-a-glance view of a patient(s) relevant medical information and indicate what has occurred or is planned to occur in the future over the course of the patient's stay.

The exemplary embodiments may visually show upon a quick glance what medical events or procedures have occurred for a patient(s). The exemplary embodiments may utilize one or more visual representations (e.g., associated with a timeline(s)) to easily and efficiently indicate relevant medical information in a summary view or picture that will enable health care professionals (e.g., nurses, therapists, doctors, etc.) to determine when a patient(s) was admitted to a medical facility as well as to identify when the patient is anticipated to be discharged from the medical facility. In this regard, the anticipated discharge may be based on a prediction. The exemplary embodiments may visually depict the discharge date of a patient as well as other pertinent medical events or procedures with respect to time and this visual depiction allows health care professionals to easily identify what events or procedures have occurred for a patient over a given time period (e.g., since the patient was admitted to an anticipated discharge from the medical facility). Additionally, the exemplary embodiments may provide one or more mechanisms that may be utilized to access information associated to a given period of time (e.g., an hour, three days, two days, etc.) to identify additional medical information related to a patient(s).

The exemplary embodiments may provide a view (e.g., a summary view) that utilizes medical information associated with one or more events or procedures, such as for example the manner in which a patient(s) has responded to certain medications, or the manner in which a patient's vital signs have responded to certain medications as well as medical information associated with surgeries, medical tests, lab results and any other suitable medical information.

In one exemplary embodiment, a corresponding method and computer program product for facilitating generation of one or more patient timelines corresponding to one or more patients are provided. The method and computer program product may include receiving medical information from one or more different computer systems. The received medical information may be associated with one or more patients. Also, the method and computer program product may include storing the received medical information and examining, via a processor, the received medical information and identifying whether data in the received medical information indicates that the medical information corresponds to one or more patients. The data may include one or more unique identifiers (IDs) associated with the patient(s). The method and computer program product also may include determining if content in the received medical information is designated for inclusion in a graphical representation(s). The content may include one or more unique codes. The method and computer program product may also include generating one or more graphical representations corresponding to a chronological sequence of medical events or procedures associated with one or more patients during a period of time.

In yet another exemplary embodiment, an apparatus is provided for facilitating generation of one or more patient timelines corresponding to one or more patients. The apparatus may include a processor configured to receive medical information from one or more different computer systems. The received medical information may be associated with one or more patients. The processor is also configured to store the received medical information and examine the received medical information and identify whether data in the received medical information indicates that the medical information corresponds to one or more patients. The data may include one or more unique identifiers (IDs) associated with the patients. The processor is also configured to determine if content in the received medical information is designated for inclusion in at least one graphical representation. The content may include one or more unique codes. Additionally, the processor may generate one or more graphical representations corresponding to a chronological sequence of medical events or procedures associated with one or more patients during a period of time.

BRIEF DESCRIPTION OF THE SEVERAL VIEWS OF THE DRAWINGS

Figure 1:
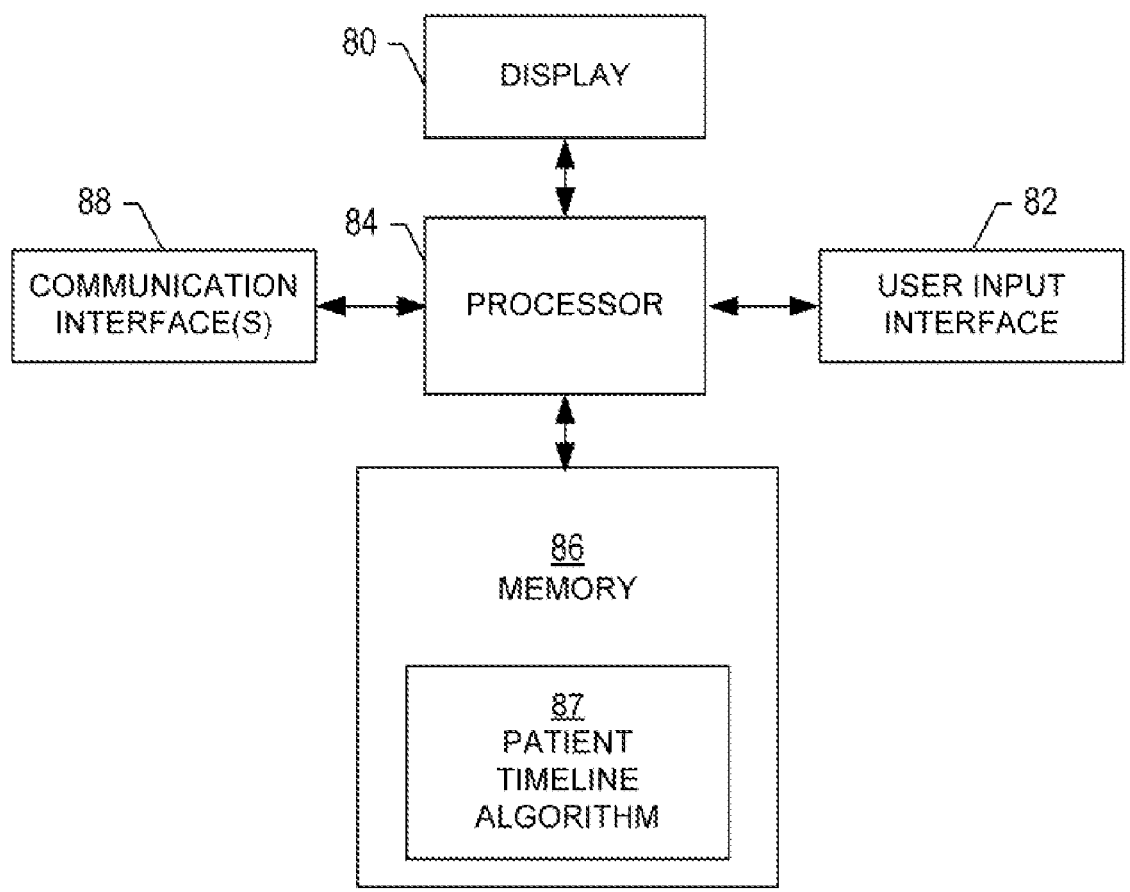
Figure 2:
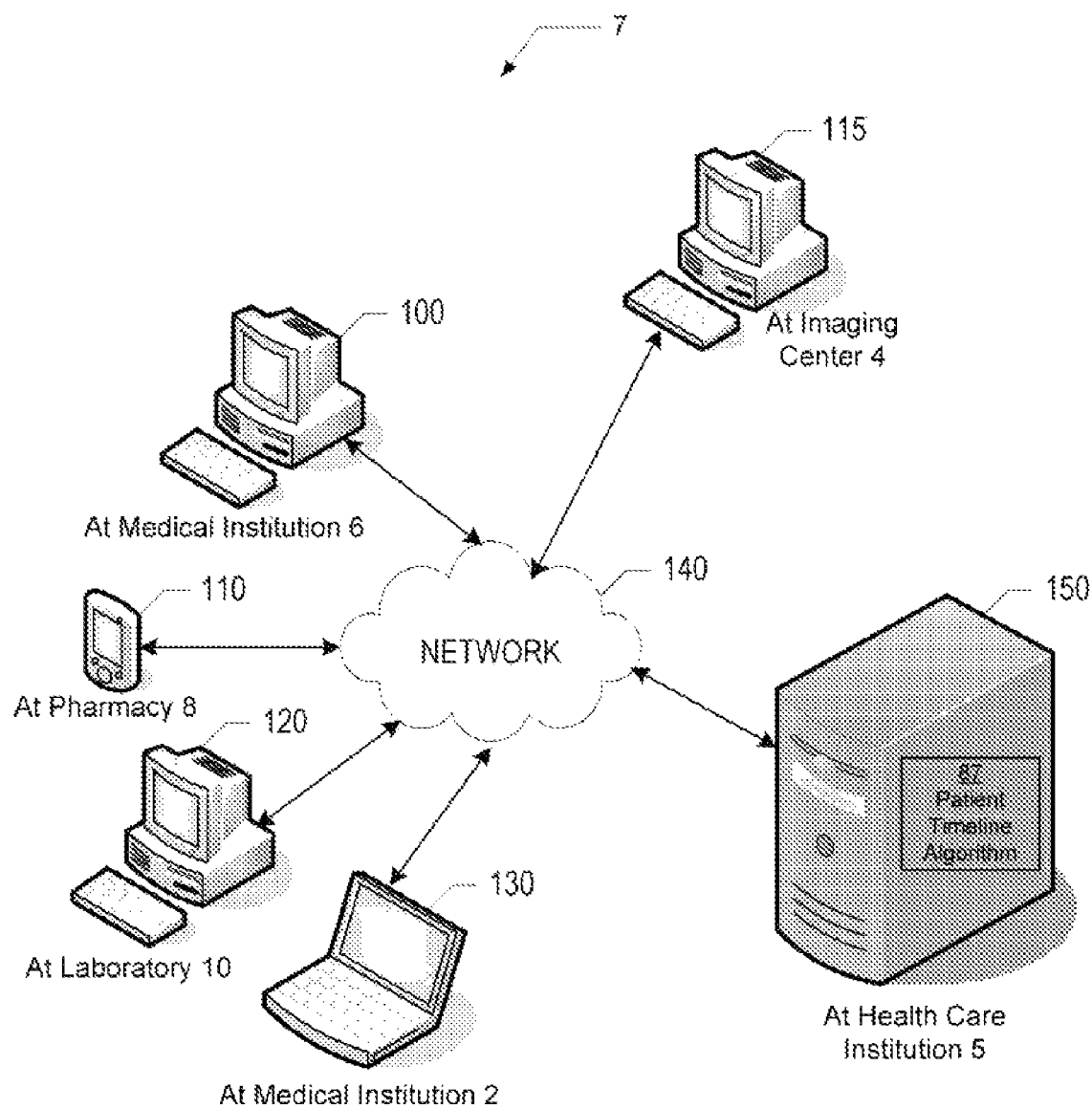
Figure 3:
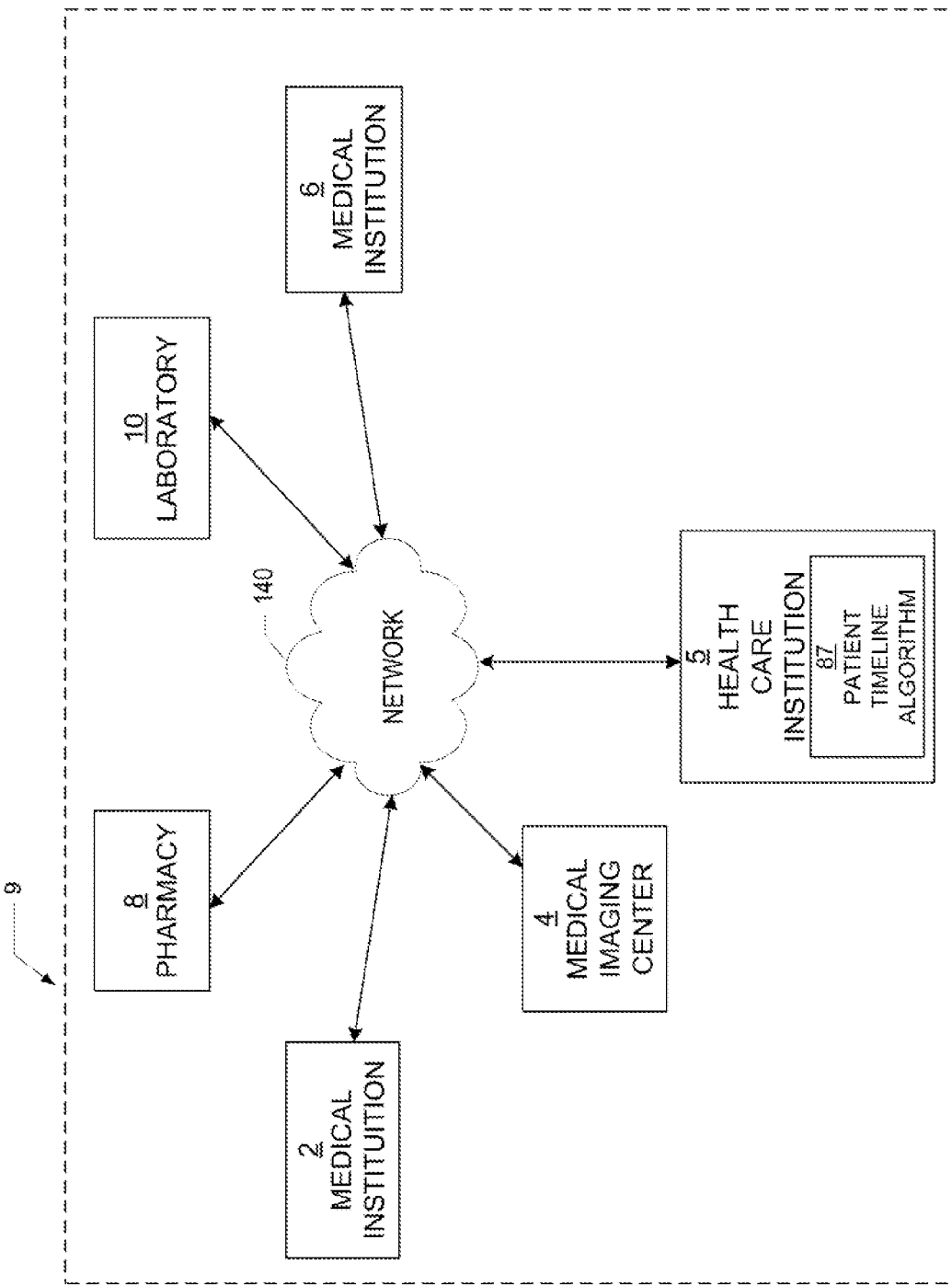
Figure 4:
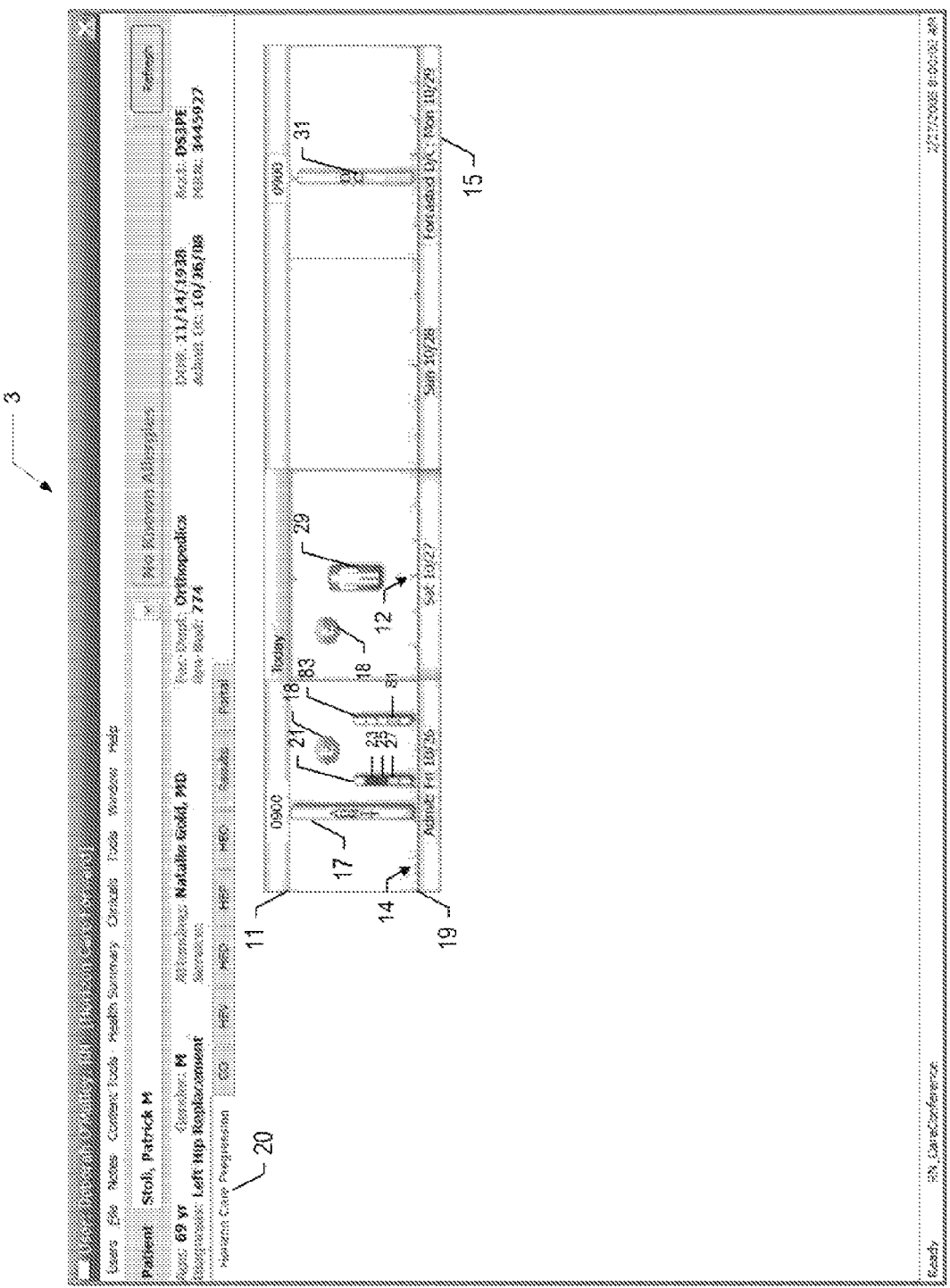
Figure 5:
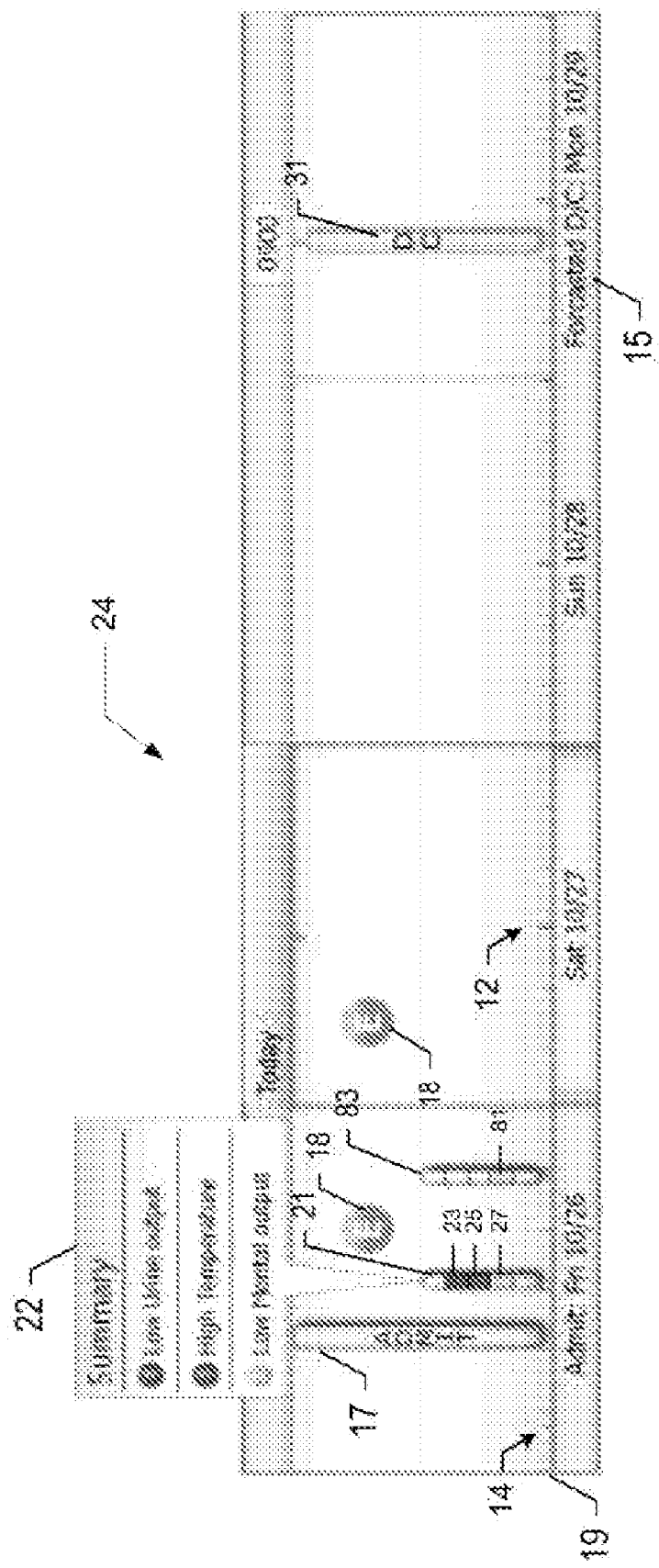
Figure 6:
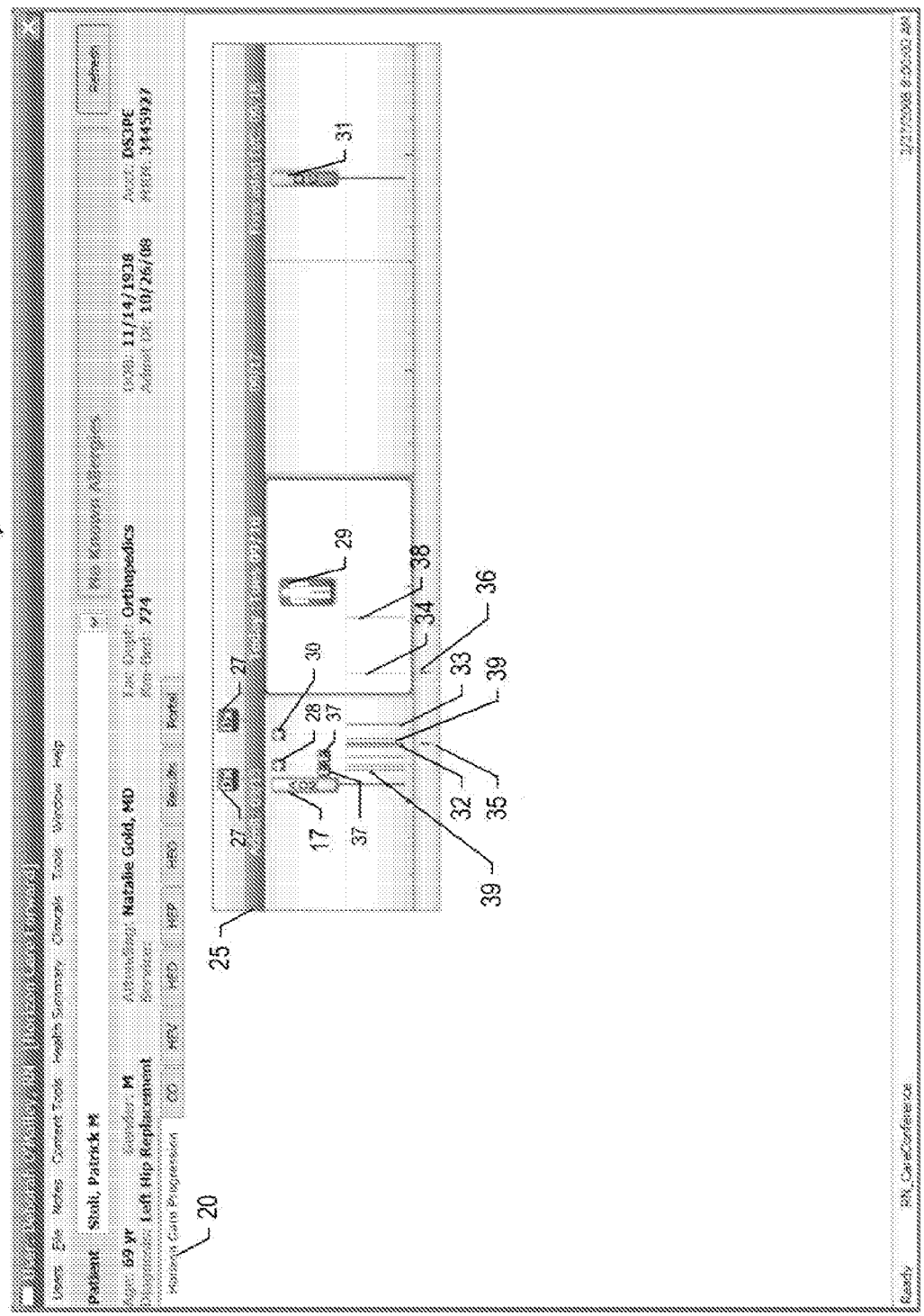
Figure 7A:
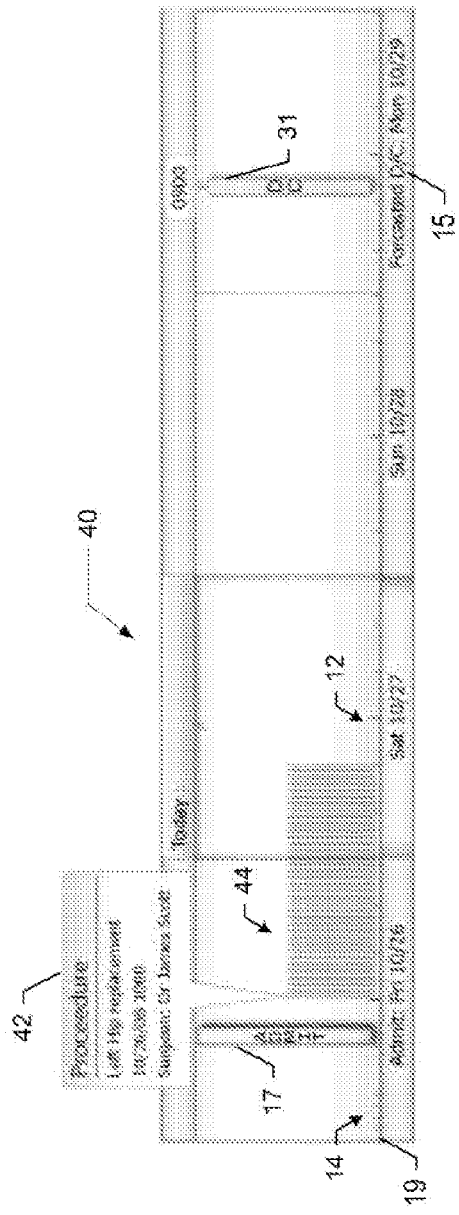
Figure 7B:
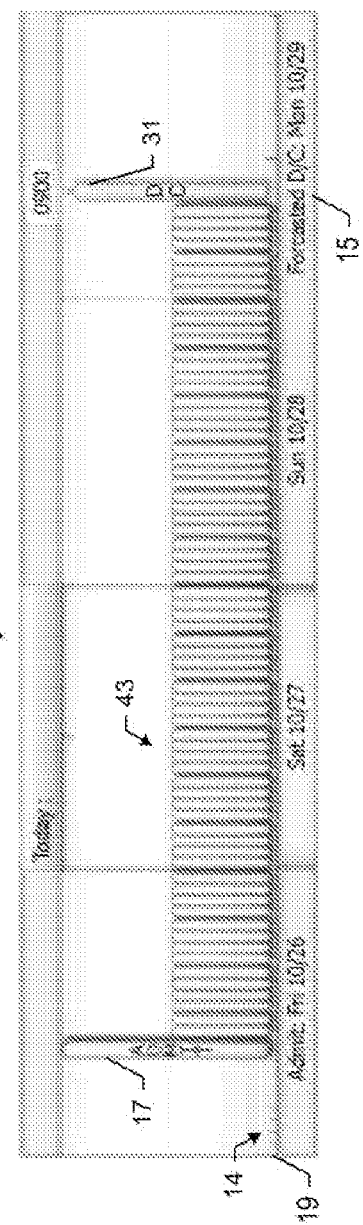
Figure 8:
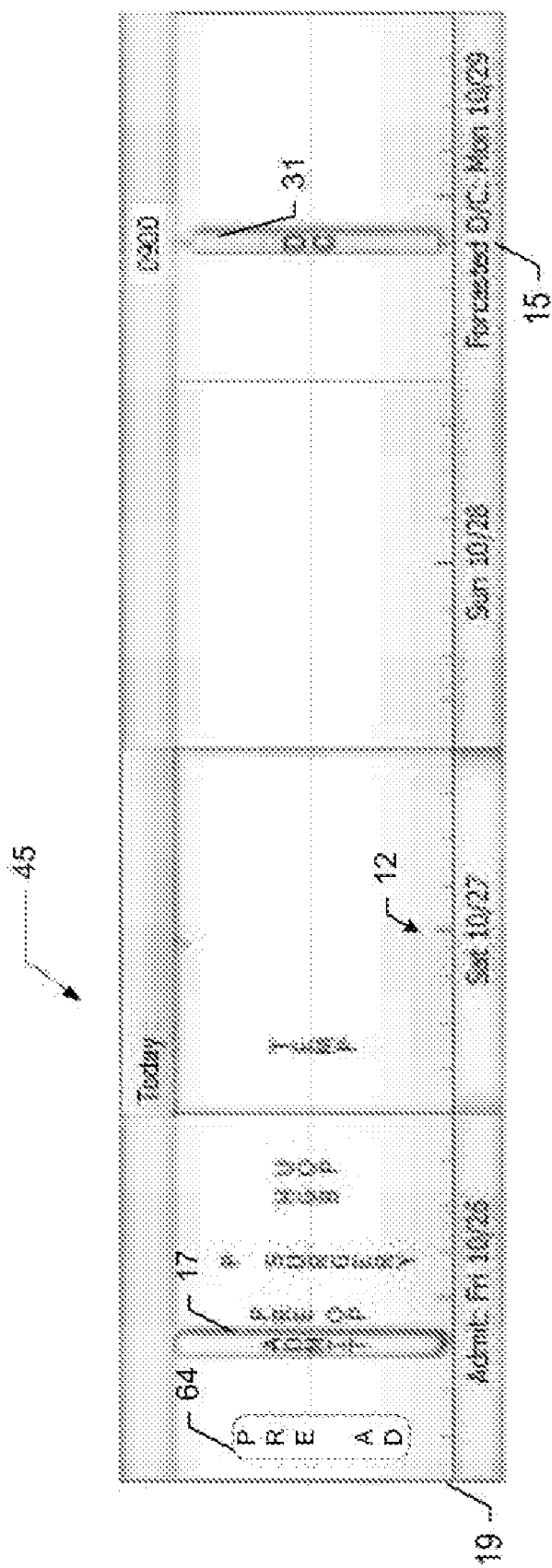
Figure 9:
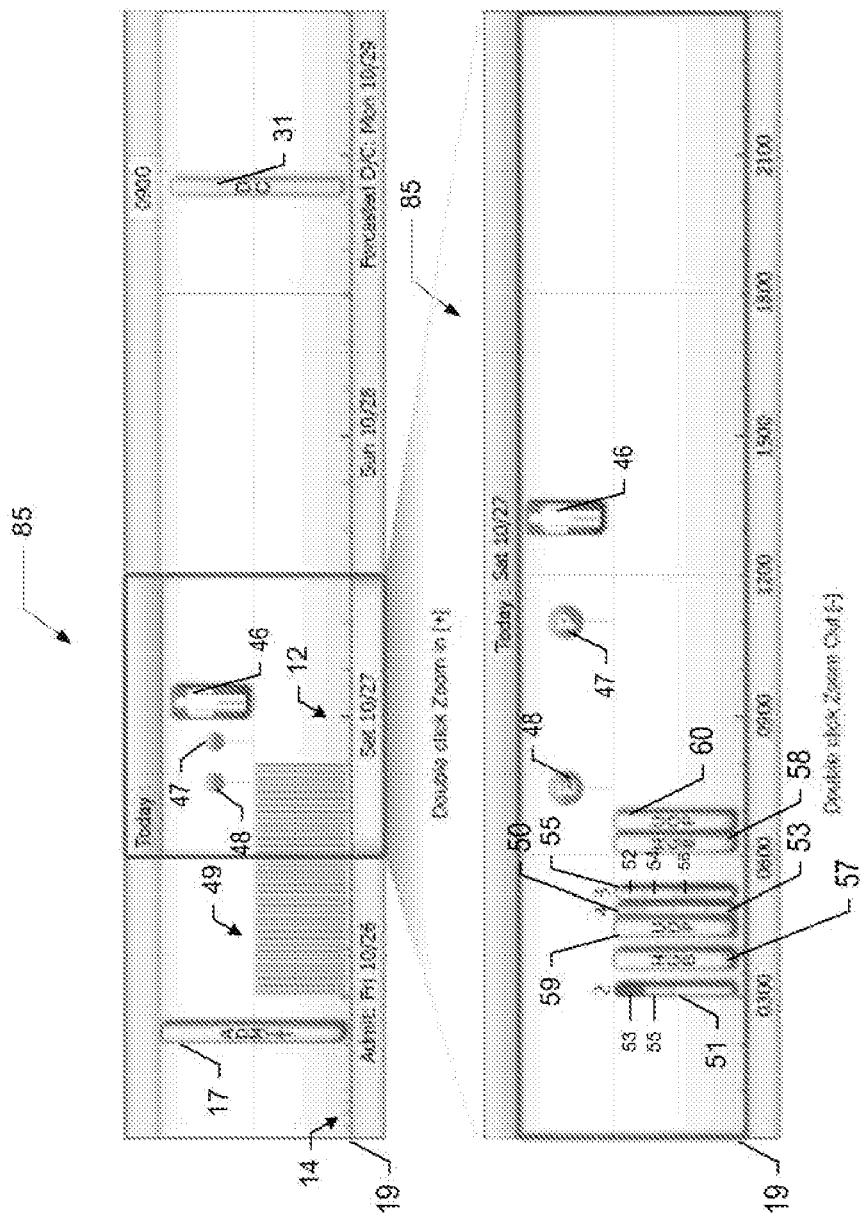
Figure 10:
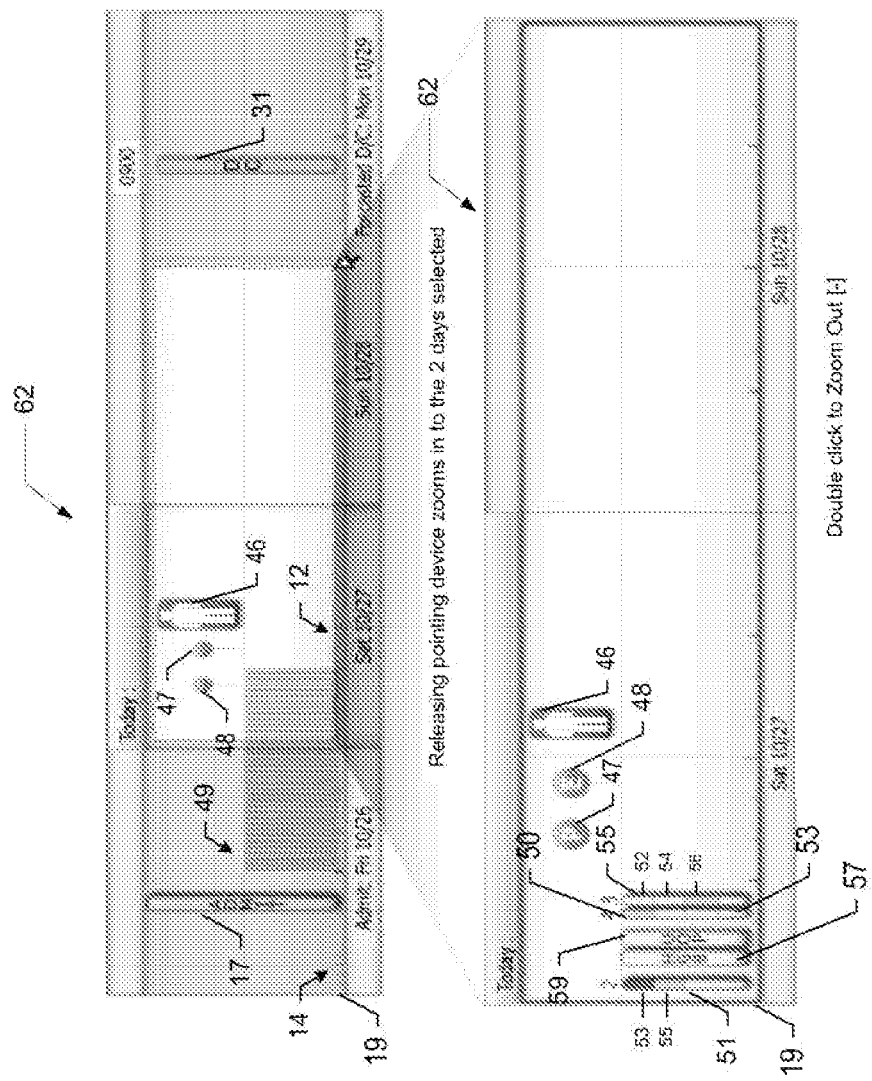
Figure 11:
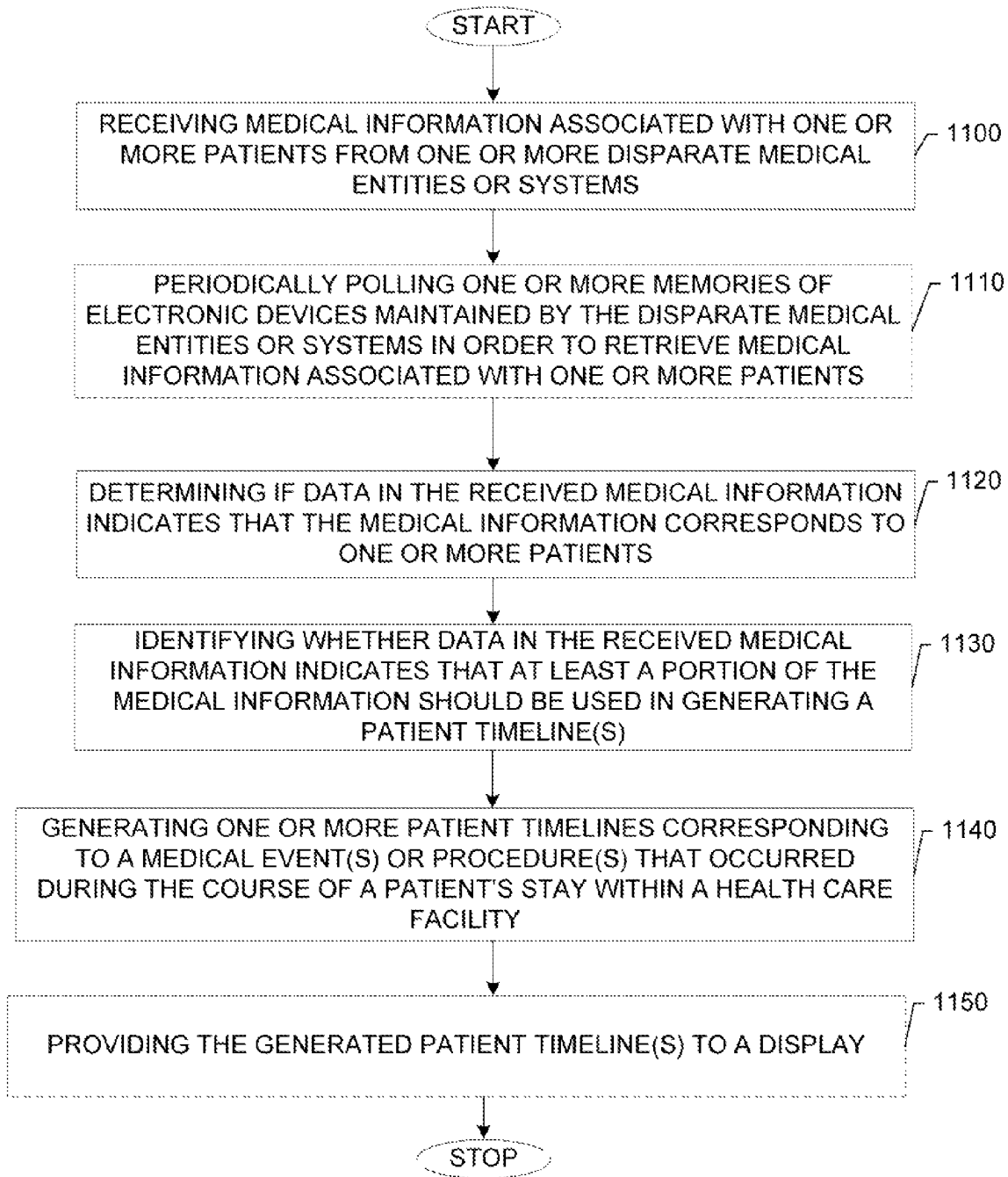

Having thus described the invention in general terms, reference will now be made to the accompanying drawings, which are not necessarily drawn to scale, and wherein:

FIG. 1 is a schematic block diagram of an electronic device according to an exemplary embodiment of the invention;

FIG. 2 is a schematic block diagram of a system for generating one or more patient timelines associated with one or more patients according to an exemplary embodiment of the invention;

FIG. 3 is a schematic block diagram of a system according to an exemplary embodiment of the invention;

FIG. 4 illustrates a patient timeline in the context of a website according to an exemplary embodiment of the invention;

FIG. 5 illustrates a patient timeline according to an exemplary embodiment of the invention;

FIG. 6 illustrates a patient timeline in the context of a website according to an exemplary embodiment of the invention;

FIGS. 7A and 7B illustrate patient timelines according to exemplary embodiments of the invention;

FIG. 8 illustrates a patient timeline according to an exemplary embodiment of the invention;

FIG. 9 illustrates an expanded portion of a patient timeline according to an exemplary embodiment of the invention;

FIG. 10 illustrates an expanded portion of a patient timeline according to an exemplary embodiment of the invention; and FIG. 11 illustrates a flowchart for facilitating generation of one or more patient timelines corresponding to one or more patients according to an exemplary embodiment of the invention.

DETAILED DESCRIPTION

The present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout. Moreover, the term "exemplary", as used herein, is not provided to convey any qualitative assessment, but instead merely to convey an illustration of an example.

FIG. 1 illustrates a block diagram of an electronic device such as a client, server, computing device (e.g., personal computer (PC), computer workstation, laptop computer, personal digital assistant, etc.) or the like that would benefit from embodiments of the invention. The electronic device includes various devices for performing one or more functions in accordance with exemplary embodiments of the invention, including those more particularly shown and described herein. It should be understood, however, that one or more of the electronic devices may include alternative devices for performing one or more like functions, without departing from the spirit and scope of the invention. More particularly, for example, as shown in FIG. 1, the electronic device can include a processor 84 connected to a memory 86. The memory can comprise volatile and/or non-volatile memory, and typically stores content, data or the like. For example, the memory may store content transmitted from, and/or received by, the electronic device. The memory is capable of storing data including but not limited to medical data such medical diagnoses, laboratory results, medical tests or measurements, medical chart information, prescription data, medical imaging data (e.g., X-rays of the human body), alert information, data associated with the admission of a patient into a medical institution and/or discharge of a patient from a medical facility or any other suitable medical data associated with one or more patients.

Also for example, the memory typically may store one or more client applications, instructions or the like that is executed by the processor 84 to perform steps associated with the operation of the electronic device in accordance with embodiments of the present invention. As explained below, for example, the memory may store one or more client application(s), for instance, software, such as for example software implementing a patient timeline algorithm 87, (also referred to herein as a patient timeline code) which may retrieve medical information associated with one or more patients from one or more different medical systems (which may operate using different computing devices) or one or more different applications within a single medical system and automatically arrange this medical information along a timeline allowing medical personnel to easily identify one or more events that have occurred or are planned to occur in the future over the course of the patient's stay within a medical facility (e.g., hospital). In this regard, the patient timeline algorithm, upon being executed by the processor 84, may generate one or more timelines containing data identifying one or more dates and specifying one or more times that one or more medical events or procedures occurred or are planned to occur in the future regarding a patient's stay within a medical facility. Additionally or alternatively, the patient timeline algorithm, upon being executed by the processor, may generate one or more timelines containing data identifying one or more dates and specifying one or more times that one or more medical events or procedures occurred or are planned to occur in the future regarding a patient's multiple stays within the medical facility over the course of the patient's lifetime. In this regard, each patient may have a profile associated with them such that over the lifetime of the patient, medical information associated with the patient may be generated with respect to a timeline relating to multiple admissions within the medical facility.

The electronic device can include one or more logic elements for performing various functions of one or more client application(s). The logic elements performing the functions of one or more client applications may be embodied in an integrated circuit assembly including one or more integrated circuits integral or otherwise in communication with a respective network entity (e.g., computing system, computing device, client, server, etc.) or more particularly, for example, a processor 84 of the respective network entity.

In addition to the memory 86, the processor 84 can also be connected to at least one interface or other means for displaying, transmitting and/or receiving data, content or the like. The interface(s) can include at least one communication interface 88 or other means for transmitting and/or receiving data, content or the like. In this regard, the communication interface 88 may include, for example, an antenna and supporting hardware and/or software for enabling communications with a wireless communication network. For example, the communication interface(s) can include a first communication interface for connecting to a first network, and a second communication interface for connecting to a second network. In this regard, the electronic device is capable of communicating with other electronic devices over a network such as a Local Area Network (LAN), Wide Area Network (WAN), Wireless Wide Area Network (WWAN), the Internet, or the like. Alternatively, the communication interface may support a wired connection with the respective network. In addition to the communication interface(s), the interface(s) may also include at least one user interface that may include one or more earphones and/or speakers, a display 80, and/or a user input interface 82. The display 80 is capable of displaying information including but not limited to medical data associated with one or more patients. In this regard, the display is capable of showing one or more timelines (also referred to herein interchangeably as patient timeline or care progression timeline), which may contain data associated one or more medical events or procedures and may indicate one or more dates and times, as well as patient admission dates and times, transfers from different medical units within a facility and corresponding date and times of such transfer, scheduled discharge dates and times, expected or forecasted discharge dates and times, one or more surgical procedures or other procedures, laboratory results, measurements, one or more pre-admission events as well as any other suitable medical information, such as tasks that remain unmet and which may be displayed at the time at which the tasks are due to be performed.

The pre-admission events may display prior to the display of the date and time of the patient's admission within the medical facility. The pre-admission events may be associated with one or more emergency care visits to a health care facility (e.g., a clinic) or any other relevant medical events that occur prior to the patient being admitted within the medical facility. The pre-admission events may span a time period of 12 months prior to the admission date of the patient or any other suitable time period prior to the admission of the patient within the medical facility.

The medical information associated with one or more patients that is shown with respect to the timelines may be retrieved from one or more different medical institutions or entities (or different medical systems, which may operate using different computing devices) or one or more applications maintained by a single medical institution or entity. Additionally, the medical information associated with the timelines that may be visible on the display may be accessible by medical personnel to access additional details regarding the medical information. The display is also capable of showing any other suitable information including but not limited to web pages associated with one or more websites. The user input interface, in turn, can comprise any of a number of devices allowing the entity to receive data from a user, such as a microphone, a keypad, keyboard, a touch display, a joystick, image capture device, pointing device (e.g., mouse), stylus or other input device.

Reference is now made to FIG. 2, which is a block diagram of an overall system that would benefit from exemplary embodiments of the invention. It should be pointed out that one or more of the components of FIG. 2 may comprise the elements of the electronic device illustrated in FIG. 1. As shown, the system 7 may include one or more electronic devices 100, 110, 115, 120, 130 (e.g., personal computers, desktop computers, laptops, personal digital assistants and the like) which may be operated by medical personnel, including but not limited to nurses, therapists, physicians, pharmacists and any other suitable health care professionals in order to access a server 150, or similar network entity, over a network 140, such as a wired or wireless local area network (LAN), a metropolitan network (MAN) and/or a wide area network (WAN) (e.g., the Internet). The electronic devices 100, 110, 115, 120 and 130 as well as the server 150 may be maintained by one or more health care institutions. For instance, the electronic device 100 may be maintained by a medical institution 6, the electronic device 110 may be maintained by a pharmacy, the electronic device 115 may be maintained by an imaging center 4 (also referred to herein as medical imaging center), the electronic device 120 may be maintained by a laboratory 10, and the electronic device 130 may be maintained by a medical institution 2. (See also e.g., FIG. 3) Additionally, the server 150 may be maintained by a health care institution 5 (also referred to herein as a health care entity). (See also e.g., FIG. 3) While five electronic devices 100, 110, 115, 120 and 130 are shown in FIG. 2, it should be pointed out that any suitable number of electronic devices may be part of the system of FIG. 2. In addition, although there is one server 150 shown in FIG. 2, it should be pointed out that any suitable number of servers may be part of the system of FIG. 2. Moreover, while a server is mentioned for purposes of illustration, its functions could be performed by many other types of computing devices without departing from the spirit and scope of the invention.

The processor of the server 150 may execute one or more algorithms or software stored in a memory. For instance, the processor of the server 150 may execute software, such as for example the patient timeline algorithm 87. In response to the processor executing the patient timeline algorithm 87, the processor may retrieve medical data associated with one or more patients from one more disparate entities such as for example medical institution 6, pharmacy 8, laboratory 10, medical institution 2, imaging center 4 or any other suitable medical entities.

The medical information that may be retrieved by the processor of the server from the medical institution 2, laboratory 10, pharmacy 8, medical institution 6 and imaging center 4 may include but is not limited to medical diagnoses, laboratory results, medical tests or measurements, medical chart information (e.g., clinician assessments, vital signs, etc.), prescription data, medical imaging data (e.g., X-rays of the human body) and alert information. The data associated with the medical diagnoses, laboratory results, medical tests or measurements, medical chart information, prescription data, medical image data and alert information may also include data corresponding dates and times this information was created or the actual dates and times of the actual events (e.g., actual date and time of a laboratory result) associated with the generation of this information. The medical information may also include but is not limited to data associated with the admission of a patient into a medical institution and a corresponding date and time of admission and/or discharge of a patient from a medical facility and corresponding date and time of admission. Additionally, the medical information may include, but is not limited to, one or more medical events or procedures (e.g., surgical procedures) and may indicate one or more dates and times of these events or procedures, transfers from different medical units (e.g., critical to telemetry, critical to medical surgery (Med-Surg), telemetry to critical, etc.) within a facility (e.g., hospital) and corresponding date and times of such transfer(s), expected or forecasted discharge dates and times, tasks that remain unmet, one or more pre-admission events and corresponding dates and times as well as any other suitable medical information. For instance, in an exemplary embodiment, the medical information may also include one or more free text entries that may be generated by utilizing a user input interface (e.g., user input interface 82) or the like.

In an exemplary embodiment, the processor of the server 150 may periodically poll the memories of the electronic devices 110, 110, 115, 120 and 130 during a predetermined time interval (e.g., every 20 minutes) to determine if there is medical information available corresponding to one or more patients and if the processor determines that medical information is available, the processor of the server may retrieve this medical information and store it in a memory of the server. In this regard, the processor of the server may utilize this medical information in generating one or more timelines associated with a patient's stay within a medical institution.

The medical information associated with one or more patients may be retrieved by the processor of the server from one or more medical entities based on one or more unique identifier (IDs) that are associated with one or more patients. For instance, a unique ID such as for example "37 24 A" may be associated with or assigned to a patient (e.g., patient Jane Doe) by the processor of the server and in this regard in response to the processor of the server determining that the medical information received or retrieved from the medical institution 2, laboratory 10, pharmacy 8, medical institution 6 and/or imaging center 4 contains this unique ID, the processor of the server may determine that the medical information (also referred to herein interchangeably as medical data or medical content) corresponds to the patient to which the unique ID was assigned (e.g., patient Jane Doe). Additionally, the medical information received by the processor of the server from the medical institution 2, laboratory 10, pharmacy 8, medical institution 6 and/or imaging center 4 may also include one or more unique codes (e.g., "7 3 12 C") which may be used by the processor of the server to determine that the medical information received by the server should be utilized in generating one or more patient timelines. It should be pointed out that the unique IDs and unique codes of the exemplary embodiments may consist of any combination of alphanumeric characters or any other suitable characters.

For example, the processor of the server may receive medical information associated with laboratory results, for example, from the laboratory 10 and this medical information may also contain data indicating a unique ID (e.g., "37 24 A") associated with a patient (e.g., patient Jane Doe) as well as a unique code (e.g., "7 3 12 C") designating that this medical information (e.g., laboratory results) should be utilized when generating a timeline(s). This medical information may also include a corresponding date and time that the laboratory results were generated as well as a date(s) and time(s) that one or more medical tests occurred and that generated the laboratory results. As another example, the processor of the server 150 may receive or retrieve medical information, such as for example information associated with a surgical procedure (e.g., hip replacement) from the medical institution 2. This medical information may also contain data indicating a unique ID (e.g., "37 24 A") associated with a patient (e.g., patient Jane Doe) as well as a unique code ("24 3 7 G") designating that this medical information should be utilized by the processor of the server in generating a display on the timeline(s). The medical information associated with the surgical procedure may also include data indicating the date(s) and time(s) that the surgical procedure occurred. In the above examples relating to the laboratory results and the surgical procedure, the processor of the server may generate a single timeline that includes data associated with both the laboratory results as well as the surgical procedure if the medical information relates to the same patient (e.g., patient Jane Doe). Alternatively, the processor of the server may generate different timelines (e.g., two different timelines) and may include the data associated with the laboratory results on one timeline (along with other relevant medical data) and the data associated with the surgical procedure on another timeline (along with other relevant medical data). It should be pointed out that the unique codes may be associated with categories of medical information. For example, a unique code such as "7 3 12 C" may be used to designate that all laboratory results are to be utilized in generating a timeline(s) and a unique code such as "24 3 7 G" may be utilized to designate that all surgical procedures are to be used by the processor of the server in generating a timeline(s), whereas a unique code such as for example "A 713 12" may be used to designate that imaging data (e.g., X-rays) are to be utilized by the processor of the server in generating a timeline(s), so on and so forth.

It should also be pointed out that medical information (admission dates and times as well as discharge dates and times, etc.) may be input directly into the server, and stored in a memory, by utilizing a keypad or the like of the user input interface (e.g., user input interface 82) and this medical information may also be utilized by the processor of the server in generating one or more timelines. The server 150 may, but need not, maintain and operate a secure access site such as a website. For instance, in response to being executed by the processor of the server, the patient timeline algorithm 87 may generate one or more timelines containing medical information and associated dates and times and these timelines may be part of a website that is maintained by the server 150. In this regard, any of the electronic devices 100, 110, 115, 120 and 130 may access information generated by the processor of the server 150 via the network 140 (e.g., Internet) in response to accessing a website or the like.

Referring now to FIG. 3, a system in which devices of FIG. 2 that are maintained and operated by entities such as for example medical institution 2, laboratory 10, pharmacy 8, medical institution 6 and imaging center 4 may be coupled to each other via network 140. The system 9 of FIG. 3 may be maintained and operated by a single entity. Alternatively, the system 9 of FIG. 3 may be maintained and operated by one or more entities. The health care institution 5 may contain a device (e.g., the processor of server 150) that executes the patient timeline algorithm 87, which may receive or retrieve medical information associated with one or more patients that may be stored and maintained at disparate medical entities, such as for example medical institution 2, laboratory 10, pharmacy 8, medical institution 6 and imaging center 4. The medical information received or retrieved (or directly input to the server 150) by the processor of the server may be utilized by the processor to generate one or more patient timelines containing medical data and associated dates and times as well as any other suitable information.

It should be pointed out that the laboratory 10 may perform one or more medical tests, medical measurements and generate one more lab results as well as medical chart information or any other suitable medical information on behalf of one more patients. The medical chart information may be any medical information that is configured and arranged to be shown in a chart (e.g., an electronic chart) so that it can be easily analyzed and identified by a health care professional (s). The pharmacy 8 may generate prescription data associated with the administration of one or more drugs in corresponding dosages or any other suitable medical data on behalf of one or more patients. The medical institution 2 and the medical institution 4 may be medical clinics or medical hospitals or other suitable health care facilities and may generate medical data associated with one or more medical procedures, diagnoses, medical tests or measurements and any other suitable medical data. The imaging center 4 may be capable of generating medical data, including but not limited to, medical images based on utilizing X-rays, ultrasound technology, magnetic resonance imaging or any other suitable mechanism to view anatomical parts of the human body or animals.

Referring to FIG. 4, an exemplary embodiment of a patient timeline is provided. The patient timeline may, but need not, be accessible via a website 3, which may be shown on a display such as for example display 80. The website may be maintained and operated by the processor of the server 150. The patient timeline 11 may show medical information and events over the course of a patient's stay within a health care facility. Utilizing the website, a user such as for example, a health care professional (e.g., a nurse, in this e.g., Deborah O'Malley, RN) may log in or sign in to the website, by utilizing a registered user name and password for example. Once access is provided to the website, the user may be provided with demographic data associated with a patient (e.g., patient Patrick M. Stoli) and other content as well as the patient timeline 11. (It should be pointed out that patient Patrick M. Stoli referred to herein denotes a fictitious person for purposes of illustration.) For instance, the user may be provided with information indicating the age of a patient (e.g., 69 yrs. old), gender (e.g., Male (M)), date of birth (DOB) (e.g., Nov. 14, 1938), date the patient was admitted to the medical facility (e.g., Oct. 26, 2008), account number (e.g., "DS3PE"), a medical record number (MRN) (e.g., "3445927"), attending physician (e.g., Natalie Gold, MD), diagnosis (e.g., Left Hip Replacement), allergy information, a medical unit in which the patient is located (e.g., Orthopedics) as well as a room/bed number (e.g., 774).

The patient timeline 11 associated with the website 3 may be generated by the processor of the server 150 upon receiving or retrieving medical information from the medical institution 2, pharmacy 8, laboratory 10, medical institution 6 or imaging center 4 as well as any medical information that is received by the server 150 by using a keyboard or the like of a user input interface of the server. In the exemplary embodiment shown in FIG. 4, the processor of the server 150 may examine information in the received or retrieved medical data and determine that a unique ID was contained in the received or retrieved medical information. In this example, the processor of the server may determine that the unique ID (e.g., "L 721 48") is associated with patient Patrick M. Stoli. Also, the processor of the server may determine that the received medical information includes data identifying a date (e.g., Friday Oct. 26, 2008) and time that a patient (e.g., patient Patrick M. Stoli) was admitted to a health care facility (e.g., health care institution 5), and may contain information associated with one or more events or procedures that occurred on a particular date(s) and time(s) while the patient is admitted to the health care facility. In the exemplary embodiment of FIG. 4, these events or procedures may relate to medical tests associated with a low urine output (UOP), a high temperature and a low mental output that occurred on a given day (e.g., Oct. 26, 2008) at specified times.

Additionally, the processor of the server may determine that the received or retrieved medical information includes data identifying one or more unique codes (e.g., "A 21 12 3", "B 10 21 24", etc.) that may be utilized by the processor to designate that corresponding medical information associated with a patient, Patrick M. Stoli in this example, is to be used by the processor of the server in generating the timeline 11. In the example of FIG. 4, the unique codes may used by the processor of the server to designate that the patient's admission date and time into the health care facility as well as the events or procedures related to the medical tests corresponding to the low urine output (UOP), the high temperature and low mental output (also referred to herein interchangeably as diminished mental status) on a day (e.g., Oct. 26, 2008) at specified times should be utilized by the processor of the server in generating the patient timeline 11.

Moreover, the processor of the server 150 may determine a forecasted or predicted discharge date 15 and time in which the patient is expected to be discharged or released from a health care facility and may determine a current date and time and include this information in the patient timeline 11. The forecasted discharge date and time may be determined using historical data, a specific diagnosis or data associated with an assigned protocol (also referred to herein as assigned medical protocol). The assigned protocol may be a medical guideline aimed at decisions regarding diagnosis, management, and medical treatment of medical conditions and may identify a time period in which patients having a certain medical condition are discharged or released from a medical facility. Additionally, based on a patient's diagnosis, the processor of the server 150 may determine the average time period in which patients with a similar diagnosis were admitted and discharged from the health care institution 5 and this average time period may be utilized as a forecasted or predicted discharge date and time. In this example, the patient Patrick M. Stoli was diagnosed as requiring a left hip replacement and the processor of the server may utilize the average time period information, or alternatively use the information associated with the assigned protocol to determine that a patient diagnosed as requiring a hip replacement is typically discharged three days from being admitted to a health care facility. As such, in the exemplary embodiment of FIG. 4, the processor of the server may determine that the forecasted or predicted discharge date of patient Patrick M. Stoli is Monday Oct. 29, 2008 at 9:00 AM, based on an average patient admission to patient discharge time of three days for conditions associated with hip replacements.

Alternatively, the processor of the server 150 may utilize the admission to patient discharge time associated with the assigned protocol to determine that the forecasted or predicted discharge date of patient Patrick M. Stoli is Monday Oct. 29, 2008 at 9:00 AM. It should be pointed out that while the time (e.g., "0900") associated with the forecasted or predicted discharge date may be shown in a military time format (i.e., a 24-hour clock notation) as provided in FIG. 4, the time associated with the forecasted or predicted discharge may also be provided based on a 12-hour clock notation (e.g., 9:00 AM).

The processor of the server may utilize the patient admission data, the events or procedures related to the medical tests corresponding to the low urine output (UOP), the high temperature and the diminished mental status and the forecasted or predicted discharge data to generate the timeline 11. In this regard, the processor of the server may generate one or more icons that are associated with dates and times to show the patient admission data, the medical event or procedures related to the medical tests corresponding to the low UOP, the high temperature, diminished mental status and the forecasted or predicted discharge data. In the exemplary embodiment of FIG. 4, these icons may be in the form of one or more capsules and the patient timeline 11 may correspond to four days (e.g., Friday October 26$^{th}$, Saturday October 27$^{th}$, Sunday October 28$^{th}$ and Monday October 29$^{th}$). While four days are shown in the patient timeline 11 of FIG. 3, it should be pointed out that any other suitable number of days may be shown or depicted in the patient timelines generated by the processor of the server 150. As shown in FIG. 4, a date (e.g., Friday October 26$^{th}$) and time (e.g., 9:00 AM) that the patient Patrick M. Stoli was admitted to the health care facility may be represented by the admit capsule 17 in relation to a time axis 19. The time axis may include major tick marks 12 which represent hours and the minor tick marks 14 each of which may represent quarter intervals (e.g., 15 minutes) within an hour. The low urine output (UOP), the high temperature and the diminished mental status data associated with the medical tests may be represented by a capsule 21. The capsule 21 may be broken into sections 23, 25 and 27 and each of these sections 23, 25 and 27 may be color coded to identify one or more medical conditions associated with a patient.

For instance, section 23 may contain a red color and this red color may be used to indicate a medical test performed on patient Patrick M. Stoli shows that he is experiencing a low urine output, section 25 may contain a red color which may be used to indicate that patient Patrick M. Stoli has a high temperature and section 27 may indicate that a medical assessment indicated that the patient Patrick M. Stoli had a diminished mental status. Also, the colors of the sections may serve to identify a medical state of urgency associated with a patient. For example, the color red may indicate a critical condition associated with a patient, whereas the color yellow may indicate a cautionary condition associated with a negative trend or medical status. The capsule 21 may be associated with date Friday October 26$^{th}$ indicating that the medical tests associated with sections 23, 25 and 27 of the capsule 21 were performed on October 26$^{th}$. Additionally, the sections 23, 25, and 27 of capsule 21 may signify that multiple events, i.e., three in this example, occurred within a given hour. Additionally, one or more events may be represented by icons 18 which are also arranged with respect to a time(s) on a given day. The icons 18 may signify the occurrence of one more other medical events including but not limited to surgeries, medical tests, diagnoses or any other suitable medical events.

Capsule 83 may represent a single medical test that was performed at some time within a given hour. The capsule 31 may have one or more sections that may be color coded. In particular, one of the sections (e.g., section 81) may contain a yellow color indicating that the results of a medical test (e.g., a test associated with detecting deep vein thrombosis (DVT)) were cautionary and represent a negative trend or status associated with patient Patrick M. Stoli. The patient icon 29 may represent a current patient location with respect to a date (e.g., Saturday October 27$^{th}$) and time in relation to a patient's admission within a health care facility and a patient's discharge from the health care facility. The Discharge (DC) capsule 31 may represent an estimated discharge date based on a diagnosis, or an assigned protocol. Visible indicia, such as for example, a color(s) within the capsule may serve to identify whether a patient(s) is on track to be discharged in a timely manner. For example, the DC capsule 31 may be colored green if the patient is on track to be discharged in a timely manner or as scheduled (e.g., there are no patient delays). Furthermore, the DC capsule 31 may be colored yellow if the patient is at risk of a delayed discharge or the DC capsule 31 may be colored red if it is presently known that the patient will not meet the expected discharge date. In the exemplary embodiment of FIG. 4, the Discharge capsule 31 may represent a forecasted or predicted discharge date (e.g., Monday October 29$^{th}$) and time (e.g. "0900" or 9:00 AM) associated with patient Patrick M. Stoli. It should be pointed out that the patient timeline 11 may be accessed by utilizing a pointing device (e.g., a mouse) to select a tab or other icon representative of the timeline, such as the Horizon Care Progression tab 20. The patient timeline 11 may show medical information and events over the course of a patient's stay within a health care facility. While the exemplary embodiment shown in FIG. 4 illustrates a website that may provide a patient timeline(s), it should be pointed out that the patient timelines may be generated and utilized by users without regard to accessing a website. For instance, the processor of the server may generate one or more patient timelines upon executing the patient timeline algorithm 87 and the patient timelines may be viewed on a display of the server 150. Additionally, while colors may be utilized in the sections of capsules to denote information associated with medical events or procedures as well as to denote a medical condition or health status of a patient, it should be pointed out that any other visible indicia may be utilized other than colors without departing from the spirit and scope of the invention. Since the colors of sections of the capsules may denote the health of a patient, the colors of the sections of the capsules may serve as alert information to a health care professional(s) informing the health care professional(s) that medical care needs to be provided to a patient.

Referring now to FIG. 5, a patient timeline 24 analogous to the patient timeline of FIG. 4 in many respects, except that the patient timeline 24 does not display patient icon 29, is provided without regard to assessing the timeline via a website. It should also be pointed out that a pointing device (e.g., mouse) of a user input interface may be utilized to have a cursor hover over any of the icons in the patient timeline 24 (or patient timeline 11) and additional information may be provided. For instance, by utilizing a pointing device or the like to position the cursor to hover over the capsule 21, summary information 22 associated with the low urine output, high temperature, and diminished mental status results may be provided and shown with respect to the timeline.

Referring now to FIG. 6, an exemplary embodiment of a patient timeline is provided. The patient timeline may, but need not, be accessible via a website 3, which may be shown on a display such as for example display 80. The website may be maintained and operated by the processor of the server 150. The patient timeline 25 may show medical information and events and procedures over the course of a patient's stay within a health care facility. For instance, the patient timeline 25 may show medical information and one or more events and procedures spanning between a patient admission date (e.g., September 15$^{th}$) and time into a health care facility to a forecasted or predicted discharge date (e.g., September 18$^{th}$) and time from the health care facility. In the exemplary embodiment of FIG. 6, the patient timeline 25 may be associated with four days (e.g., September 15$^{th}$, September 16$^{th}$, September 17$^{th}$, and September 18$^{th}$). However, the patient timeline 25 may be associated with any suitable number of days without departing from the spirit and scope of the invention. The diagnosis (Dx) icons 27 may represent that a patient (e.g., Patrick M. Stoli) received two different diagnoses (e.g., patient needs a left hip replacement and patient has a torn medial collateral ligament (MCL) at different times on a given date (e.g., September 15$^{th}$).

The arrows 28 and 30 may represent that a patient (e.g., patient Patrick M. Stoli) was transferred between medical units of a health care facility. For example, arrow 28 may indicate that patient Patrick M. Stoli was transferred from the orthopedics medical unit to an intensive care unit (ICU) and arrow 30 may represent that patient Patrick M. Stoli was transferred from the ICU to a surgical unit. The icons 37 may represent that additional data may be accessed regarding one more events or procedures associated with a patient. The patient timeline 25 may be associated with one or more markers (also referred to herein interchangeably as capsules). These markers may be associated with distinctive visible indicia, such as colors, indicative of the relative priority with which the patient is to be treated or otherwise providing information regarding the status of the patient or the treatment of the patient. For instance, marker 32 may contain a red color which may represent any critical or highly urgent medical event (e.g., significant loss of blood), and marker 34 may contain a yellow color which may represent a medical event (e.g., diminished mental status of a patient) that has a negative trend or status and may indicate that the event is of importance but may not immediately be life threatening. The markers 33, 38 and 39 may contain a gray color which may represent that one or more medical events or procedures (e.g., left hip replacement surgery) have been performed on time and completed within a predetermined time period. For instance, marker 33 may represent that an event such as for example, a left hip replacement surgery for patient Patrick M. Stoli was performed at a scheduled time (e.g., 9:00 AM on September 15$^{th}$) and completed within a predetermined time period, such as for example, within 4 hours of the scheduled time (e.g., 1:00 PM). The exclamation marks 35 and 36 may serve as supplemental indicators to show additional details for the thin markers. Showing an exclamation mark(s) (e.g., exclamation mark 35) below a marker(s) (e.g., marker 32) helps to accommodate the size of the ultra compact marker foot print, which may be too small to contain any text. Also, the exclamation marks 35 and 36 may represent that the event(s) associated with the marker (e.g., marker 34) requires medical attention by a health care professional (e.g., doctor, nurse, therapists, etc.). The marker(s) (e.g., marker 32) of the patient timeline 25 associated with the color red may indicate medical events or procedures that are the most urgent whereas markers associated with the color yellow may indicate that medical events or procedures are less urgent than the events or procedures associated with red markers but are still of high importance and require some level of medical attention by a health care professional(s).

Referring now to FIG. 7A, another exemplary embodiment of a patient timeline is provided. The patient timeline 40 of FIG. 7A shows a plurality of markers 44, an admit capsule 17 and a discharge capsule 31. The markers 44 may represent that three medical events or procedures occurred every 15 minutes during a given time period (e.g., between 10:00 AM on Friday October 26$^{th}$ and 9:00 AM on Saturday October 27$^{th}$). In this regard, three markers per minor tick marks 14 may be shown during a time period (e.g., between 10:00 AM on Friday October 26$^{th}$ and 9:00 AM on Saturday October 27$^{th}$) associated with the markers 44 on the timeline 40. Additionally, by utilizing a pointing device (e.g., mouse) or the like, a user can access additional information linked to or associated with each of the markers. For instance, in response to hovering over one of the markers, the processor of the server may cause patient procedure information 42 to be shown indicating that a patient such as for example patient Patrick M. Stoli, had a surgical procedure relating to a left hip replacement on Oct. 26, 2008 at 10:00 AM and may contain data indicating that the doctor James Scott performed this surgical procedure.

Referring to FIG. 7B, another exemplary embodiment of a patient timeline is provided. The patient timeline 41 includes an admit capsule, a discharge capsule 31 and a plurality of capsules 43. The plurality of capsules 43 are arranged with respect to dates and time along the time axis 19. Each of the capsules 43 may represent that one medical event or procedure occurred each hour after a patient was admitted to a health care facility up to a forecasted or predicted discharge date and time (e.g., Monday October 26$^{th}$ at 9:00 AM) that the patient was expected to be released from the health care facility.

Referring now to FIG. 8, an exemplary embodiment of a patient timeline is provided. The patient timeline 45, may include an admit capsule 17, a discharge capsule 31 and text associated with one or more events or procedures that occurred at specific dates and times. Additionally, the patient timeline 45 may optionally include a pre-admission (Pre Ad) capsule 62 associated with one or more medical events (e.g., medical tests or lab tests, etc.) that occurred prior to a patient's admission to a health care facility. In this regard, the patient timeline 45 indicates that a pre-operative procedure ("PRE OP"), a surgical procedure ("P SURGERY"), a hemoglobin ("HGB") test and a urine output ("UOP") measurement were performed for a given a patient at specified times on Friday October 26th. Additionally, the patient timeline 45 may include data indicating that a temperature measurement regarding a patient was performed on Saturday October 27th and the temperature is elevated.

Referring now to FIG. 9, an exemplary embodiment of a patient timeline is provided. The patient timeline 85 of FIG. 9 may include an admit capsule 17, a discharge capsule 31, a patient icon 46, an event icon 48, a procedure icon 47 and a plurality of markers 49 (also referred to herein as a plurality of capsules 49). The plurality of markers 49 may represent three medical events that occurred every 15 minutes per hour during a time period associated with the markers 49. It should be pointed out that the dates and times in the timelines of the exemplary embodiments may be zoomed in on or zoomed out from and corresponding areas of the timelines may be displayed in a compact or expanded state, respectively. In this regard, a user such as for example a health care professional may utilize a pointing device (e.g., mouse) or the like of a user input interface (e.g., user input interface 82) to access data corresponding to a particular time period on the patient timeline 85. For instance, a user may move the pointing device over (or hover over) a particular portion (e.g., a portion associated with Saturday October 27$^{th}$) of the timeline 85. The pointing device may be utilized to double click the portion of the timeline that the pointing device is hovering over, in this example the portion of the timeline 85 associated with Saturday October 27$^{th}$. Double clicking the portion of the patient timeline that the pointing device may be hovering over may invoke or trigger the processor of the server 150 to zoom in on this portion of the patient timeline 85.

For instance, in the exemplary embodiment of FIG. 9, in response to the portion of the timeline 85 associated with Saturday October 27$^{th}$ being double clicked, the processor of the server may zoom in on information and time periods associated with Saturday October 27$^{th}$. In this regard, the zoomed in portion of the patient timeline may show each hour (e.g., 0000 hrs. to 2400 hrs.) within a 24 hour period for Saturday October 27$^{th}$. Also the zoomed in portion of the patient timeline 85 may show multiple events or procedures per hour. Between the hours of 3:00 AM and 4:00 AM, three medical events or procedures may be shown. Two of these events or procedures may be associated with capsule 51 and a number, two in this example, may be placed above the capsule 51 indicating that the capsule is associated with two medical events or procedures. These two events or procedures may be denoted by section 53 and section 55 within the capsule 51. Section 53 may be associated with visible indicia indicating the status of a medical event (e.g., a medical test(s) or measurement(s)) as well as the status of a patient's health in relation to the medical event. The visible indicia may, but need not, consist of one or more colors. For instance, section 53 may contain a red color indicating a patient's blood pressure, for example, is in a critical condition and the red color may also denote to a health care professional that the patient is in urgent need of medical attention. Additionally, section 55 may contain a yellow color indicating that a patient's mental capacity is diminished, for example, and the yellow color may also denote that the patient's health is deteriorating or showing a negative trend and that the patient requires medical attention, although the urgency of the medical attention is less than the urgency associated with a section of a capsule having a red color.

Capsule 57 may indicate that a medical test or measurement associated with hemoglobin (HGB) occurred between the hours of 3:00 AM and 4:00 AM on Saturday October 27$^{th}$ for a given patient. Capsule 57 may contain a gray color indicating that results of the medical test or measurement associated with HGB was normal for a given patient. The capsule 59 may indicate that a medical test or measurement associated with a patient's urine output (UOP) occurred between the hours of 4:00 AM and 5:00 AM and the capsule 59 may contain a color gray indicating that the results of the medical test or measurement associated with the UOP was normal for a given patient. Capsule 53 may be associated with a number, for example number 4, located above the capsule indicating that the capsule 53 represents the occurrence of four medical events or procedures. In this regard, the capsule 53 may be divided into four sections and one section 50 of the capsule 53 may denote that a medical test associated with DVT was performed during the hours between 4:00 AM and 5:00 AM and may contain a yellow color indicating that the results of the medical test represent a deteriorating health condition of a patient requiring medical attention. Each of the other three sections of capsule 53 may denote a medical event, for example a medical test and may contain a gray color indicating that the results of these tests were normal.

Capsule 55 may be associated with a number, three in this example, which may be placed above capsule 55 indicating that the capsule is associated with three medical events or procedures that occurred during the hours of 5:00 AM and 6:00 AM. In this regard, capsule 55 may contain sections 52, 54 and 56 which may denote the occurrence of a medical event or procedure such as for example a medical test or measurement. For instance, section 56 may denote that a patient experienced significant levels of blood loss and in this regard section 56 may contain a yellow color indicating that a patient's health is deteriorating and is indicative of a negative trend or status. Section 52 and section 54 may each denote that a medical test was performed on a patient and may contain a gray color indicating that the results of the medical tests were normal.

Capsules 58 and 60 may indicate that two medical events or procedures occurred during the hours between 6:00 AM and 7:00 AM for a given patient. In this regard, capsule 58 may indicate that a medical test to detect levels of hemoglobin (HGB) for a given patient was performed. Capsule 60 may indicate that a medical test associated with a urine output (UOP) was performed on the patient. Additionally, capsules 58 and 60 may contain a gray color indicating that the results of the medical tests associated with capsules 58 and 60 were normal.

The patient icon 46 may represent a current patient location with respect to a date (e.g., Saturday October 27$^{th}$) and time in relation to a patient's admission within a health care facility and a patient's discharge from the health care facility. It should be pointed out that the zoomed in portion of the patient timeline 85 may illustrate an expanded view of the event icon 48 and the procedure icon 47 and in this regard a letter "E" may be shown in the event icon 48 and a letter "P" may be shown in procedure icon 47.

By utilizing the pointing device of a user input interface for example, a user may double click the zoomed in portion of the patient timeline (e.g., portion corresponding to Saturday October 27$^{th}$) to zoom out and show a compacted version of the applicable portion of the patient timeline 85. It should also be pointed out that while the capsules and markers of the exemplary embodiments have been described as having red, yellow and gray colors any other suitable colors or visible indicia may be used to convey medical results and the health of a patient without departing from the spirit and scope of the invention.

Referring now to FIG. 10, an exemplary embodiment of a patient timeline is provided. A user may utilize a pointing device (e.g., mouse) or the like to select one or more days on the patient timeline 62 in order to zoom in and view an expanded version of the selected day(s). For instance, a user may utilize a pointing device or the like to click and drag the pointing device across an area of the timeline 62 related to October 27 to an area of the timeline 62 associated with Sunday October 28$^{th}$ so that the entire viewable area corresponding to Saturday October 27$^{th}$ and Sunday October 28$^{th}$ is selected. Upon releasing the pointing device an expanded version of the patient timeline 62 corresponding to two days, namely Saturday October 27$^{th}$ and Sunday October 28$^{th}$ may be shown.

It should be pointed out that each of the timelines described herein may pertain to a single patient. However, patient timelines corresponding to one or more patients may be utilized and employed without departing from the spirit and scope of the invention.

Referring now to FIG. 11, a flowchart for facilitating the generation of one or more patient timelines according to an exemplary embodiment is provided. At operation 1100, a device such as for example a processor of a server (e.g., server 150) may receive medical information associated with one more patients from one or more disparate medical entities or medical systems, each of which may utilize different computer systems. The disparate medical systems or medical entities may consist of medical institution 2, laboratory 10, pharmacy 8, medical institution 6 and medical imaging center 4. Optionally, at operation 1110, a device such as a processor of a server may periodically poll one or more memories of the electronic devices maintained by disparate medical entities (e.g., medical institution 2, laboratory 10, pharmacy 8, medical institution 6 and medical imaging center 4) in order to retrieve medical information associated with one or more patients. At operation 1120, the processor of the server may examine the received medical information sent from the disparate medical entities or systems and identify whether the data in the medical information corresponds to one or more patients. The data used to identify one or more patients may correspond to a unique identifier (ID).

At operation 1130, the processor of the server may determine or identify whether data in the received medical information indicates that at least a portion of the medical information should be used by the processor of the server in generating one or more patient timelines containing data corresponding to one or more medical events or procedures associated with a patient(s) during the patient's stay within a health care facility. The data used to determine whether a portion of the received medical information should be used in generating a patient timeline may be a unique code. At operation 1140, the processor of the server 150 may utilize at least a portion of the received medical information to generate one or more patient timelines containing one or more medical events or procedures that occurred during the course of a patient's stay within a health care facility.

Optionally, at operation 1150, the processor of the server may provide the generated patient timeline(s) to a display of a device. In this regard, a health care professional(s) may view the generated patient timeline and evaluate relevant medical information pertaining to a patient's health.

It should be understood that each block or step of the flowchart shown in FIG. 11 and combination of blocks in the flowchart, can be implemented by various means, such as hardware, firmware, and/or software including one or more computer program instructions. For example, one or more of the procedures described above may be embodied by computer program instructions. In this regard, the computer program instructions which embody the procedures described above may be stored by a memory of the electronic devices as well as the server and executed by a processor in the electronic device(s) and/or the network entities, e.g., server. As will be appreciated, any such computer program instructions may be loaded onto a computer or other programmable apparatus (i.e., hardware) to produce a machine, such that the instructions which execute on the computer or other programmable apparatus (e.g., hardware) means for implementing the functions implemented specified in the flowcharts block(s) or step(s). These computer program instructions may also be stored in a computer-readable memory that can direct a computer or other programmable apparatus to function in a particular manner, such that the instructions stored in the computer-readable memory produce an article of manufacture including instruction means which implement the functions specified in the flowcharts block(s) or step(s). The computer program instructions may also be loaded onto a computer or other programmable apparatus to cause a series of operational steps to be performed on the computer or other programmable apparatus to produce a computer-implemented process such that the instructions which execute on the computer or other programmable apparatus provide steps for implementing the functions that are carried out in the system.

The above described functions may be carried out in many ways. For example, any suitable means for carrying out each of the functions described above may be employed to carry out the invention. In one embodiment, all or a portion of the elements of the invention generally operate under control of a computer program product. The computer program product for performing the methods of embodiments of the invention includes a computer-readable storage medium, such as the non-volatile storage medium, and computer-readable program code portions, such as a series of computer instructions, embodied in the computer-readable storage medium.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method comprising:
receiving medical information from one or more different computer systems;
storing the received medical information;
examining, via a processor, the received medical information and identifying whether data in the received medical information indicates that the medical information corresponds to a patient, the data comprising a unique identifier associated with the patient;
evaluating a unique code associated with content in the received medical information to determine whether the content is designated for inclusion in at least one graphical representation;
generating a graphical representation corresponding to a chronological sequence of medical events or procedures associated with the patient during a period of time, the graphical representation is generated based at least in part on evaluation of the unique code, wherein the graphical representation comprises a timeline comprising a time axis corresponding to one or more dates and times associated with the occurrence of one or more medical events or procedures associated with the patient;
determining a predicted discharge date of the patient from a health care facility based at least in part on the received medical information;
including the predicted discharge date in the graphical representation as an endpoint to the timeline; and
including an indication of a health event associated with the patient that occurs before the admission date in the graphical representation as an initial point to the timeline.

2. The method of claim 1, further comprising displaying the graphical representation.

3. The method of claim 1, wherein the period of time comprises a time between the health event that occurs before the admission date in which the patient is admitted to the health care facility and the predicted discharge date in which the patient is to be released from the health care facility in the future.

4. The method of claim 3, further comprising determining the predicted discharge date on the basis of historical data associated with a medical condition or on the basis of an assigned medical protocol.

5. The method of claim 1, wherein receiving comprises polling one or more of the different computer systems at predetermined time intervals to receive the medical information.

6. The method of claim 1, wherein the graphical representation comprises an item of visible indicia associated with and indicating the occurrence of each of two or more medical events or procedures, at least one of the items of visible indicia providing details regarding an actual medical event associated with the patient.

7. The method of claim 6, wherein the items of visible indicia comprise one or more graphical icons and wherein at least one of the icons comprises data associated with a plurality of medical events or procedures that occurred within a particular time period.

8. The method of claim 6, further comprising generating at least one of the items of visible indicia to indicate a level of medical care to be provided to the patient by a health care professional.

9. The method of claim 6, further comprising generating at least one of the items of visible indicia to indicate a current medical condition associated with the patient.

10. The method of claim 9, wherein the medical condition is associated with information indicating at least one of a medical diagnosis, or one or more medical test results associated with the patient.

11. An apparatus comprising a processor configured to:
receive medical information, associated with one or more patients, from one or more different computer systems;
store the received medical information;
examine the received medical information and identify whether data in the received medical information indicates that the medical information corresponds to a patient, the data comprising a unique identifier associated with the patient;
evaluate a unique code associated with content in the received medical information to determine whether the content is designated for inclusion in at least one graphical representation;
generate a graphical representation corresponding to a chronological sequence of medical events or procedures associated with the patient during a period of time, the graphical representation is generated based at least in part on evaluation of the unique code, wherein the graphical representation comprises a timeline comprising a time axis corresponding to one or more dates and times associated with the occurrence of the medical events or procedures associated with the patient;
determine a predicted discharge date of the patient from a health care facility based at least in part on the received medical information;
include the predicted discharge date in the graphical representation as an endpoint to the timeline; and
include an indication of a health event associated with the patient that occurs before the admission date in the graphical representation as an initial point to the timeline.

12. The apparatus of claim 11, wherein the processor is further configured to provide the graphical representation to at least one display.

13. The apparatus of claim 11, wherein the period of time comprises a time between the health event that occurs before the admission date in which the patient is admitted to the health care facility and the predicted discharge date in which the patient is to be released from the health care facility in the future.

14. The apparatus of claim 13, wherein the processor is further configured to determine the predicted discharge date on the basis of historical data associated with a medical condition or on the basis of an assigned medical protocol.

15. The apparatus of claim 11, wherein the processor is configured to receive by polling one or more of the different computer systems at predetermined time intervals to receive the medical information.

16. The apparatus of claim 11, wherein the graphical representation comprises an item of visible indicia associated with and indicating the occurrence of each of two or more medical events or procedures, at least one of the items of visible indicia providing details regarding an actual medical event associated with the patient.

17. The apparatus of claim 16, wherein the items of visible indicia comprises one or more graphical icons and wherein at least one of the icons comprises data associated with a plurality of medical events or procedures that occurred within a particular time period.

18. The apparatus of claim 16, wherein the processor is further configured to generate at least one of the items of visible indicia to indicate a level of medical care to be provided to the patient by a health care professional.

19. The apparatus of claim 16, wherein the processor is further configured to generate at least one of the items of visible indicia to indicate a current medical condition associated with the patient.

20. The apparatus of claim 19, wherein the medical condition is associated with information indicating at least one of a medical diagnosis, or one or more medical test results associated with the patient.

21. A computer program product, the computer program product comprising at least one non-transitory computer-readable storage medium having computer-readable program code portions stored therein, the computer-readable program code portions comprising:
a first executable portion for receiving medical information, associated with one or more patients, from one or more different computer systems;
a second executable portion for storing the received medical information;
a third executable portion for examining, via a processor, the received medical information and identifying whether data in the received medical information indicates that the medical information corresponds to a patient, the data comprising a unique identifier associated with the patient;
a fourth executable portion for evaluating a unique code associated with content in the received medical information to determine whether the content is designated for inclusion in at least one graphical representation;
a fifth executable portion for generating a graphical representation corresponding to a chronological sequence of medical events or procedures associated with the patient during a period of time, the graphical representation is generated based at least in part on evaluation of the unique code, wherein the graphical representation comprises a timeline comprising a time axis corresponding to one or more dates and times associated with the occurrence of the medical events or procedures associated with the patient;
a sixth executable portion for determining a predicted discharge date of the patient from a health care facility based at least in part on the received medical information;
a seventh executable portion for including the predicted discharge date in the graphical representation as an endpoint to the timeline; and
an eighth executable portion for including an indication of a health event associated with the patient that occurs before the admission date in the graphical representation as an initial point to the timeline.

22. The computer program product of claim 21, wherein the graphical representation comprises an item of visible indicia associated with and indicating the occurrence of each of two or more medical events or procedures associated with the patient, at least one of the items of visible indicia providing details regarding an actual medical event associated with the patient.

* * * * *